(12) United States Patent
Weigand

(10) Patent No.: US 9,779,909 B2
(45) Date of Patent: Oct. 3, 2017

(54) APPARATUS AND METHOD FOR GENERATING X-RAY RADIATION

(75) Inventor: Frank Weigand, Heidenheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 342 days.

(21) Appl. No.: 14/235,239

(22) PCT Filed: Jul. 24, 2012

(86) PCT No.: PCT/EP2012/064509
§ 371 (c)(1),
(2), (4) Date: Jun. 9, 2014

(87) PCT Pub. No.: WO2013/014161
PCT Pub. Date: Jan. 31, 2013

(65) Prior Publication Data
US 2014/0328467 A1 Nov. 6, 2014

Related U.S. Application Data

(60) Provisional application No. 61/572,940, filed on Jul. 25, 2011.

(30) Foreign Application Priority Data

Jul. 25, 2011 (DE) .......................... 10 2011 108 508

(51) Int. Cl.
H01J 35/30 (2006.01)
H01J 35/14 (2006.01)
(Continued)

(52) U.S. Cl.
CPC ............ *H01J 35/14* (2013.01); *A61N 5/1001* (2013.01); *H01J 35/30* (2013.01); *H01J 35/32* (2013.01)

(58) Field of Classification Search
CPC ...... A61N 5/001; H01J 35/14; H01J 35/30;qa H01J 35/321
(Continued)

(56) References Cited

U.S. PATENT DOCUMENTS 5,647,663 A 7/1997 Holmes
6,421,416 B1 7/2002 Sliski et al.
(Continued)

FOREIGN PATENT DOCUMENTS

CN 1144015 A 2/1997
CN 1853566 A 11/2006
(Continued)

OTHER PUBLICATIONS

International Preliminary Report on Patentability mailed Feb. 6, 2014, from PCT Application No. PCT/EP2012/064509.
(Continued)

*Primary Examiner* — Courtney Thomas
(74) *Attorney, Agent, or Firm* — Kriegsman & Kriegsman

(57) ABSTRACT

The present invention relates to an apparatus (10) as well as a method for generating X-ray radiation, in particular for generating an X-ray radiation field, comprising an electron source (11) for generating an electron beam (12) as well as a target (13) for generation of X-ray radiation, in particular of an X-ray radiation field by electrons of the electron beam (12) impinging on the target (13). The present invention is characterized in that, the apparatus (10) is designed for generating an adjustable and/or changeable X-ray radiation, in particular for generating an adjustable and/or changeable X-ray radiation field, and in that the apparatus (10) has a variation appliance (15) for varying of at least one parameter of the electron beam source (11) and/or the electron beam (12) for influencing the X-ray radiation, in particular the X-ray radiation field.

14 Claims, 2 Drawing Sheets

(51) Int. Cl.
*A61N 5/10* (2006.01)
*H01J 35/32* (2006.01)

(58) Field of Classification Search
USPC .................................................. 378/119–144
See application file for complete search history.

(56) References Cited

U.S. PATENT DOCUMENTS

| | | | |
|---|---|---|---|
| 8,724,775 B2 | 5/2014 | Kleinwaechter et al. | |
| 2004/0101110 A1* | 5/2004 | Eppler | G01N 23/04 378/207 |
| 2008/0095317 A1* | 4/2008 | Lemaitre | H01J 35/04 378/138 |
| 2008/0137805 A1 | 6/2008 | Forster et al. | |
| 2009/0154650 A1* | 6/2009 | Tanabe | A61N 5/1042 378/137 |
| 2011/0105822 A1* | 5/2011 | Roeder | A61M 25/10 600/1 |
| 2014/0112441 A1* | 4/2014 | Becker | A61B 6/032 378/62 |
| 2014/0233706 A1 | 8/2014 | Weigand | |

FOREIGN PATENT DOCUMENTS

| | | |
|---|---|---|
| DE | 102005018330 A1 | 10/2006 |
| DE | 102006043551 A1 | 3/2008 |
| DE | 102009014693 A1 | 12/2010 |
| DE | 102010036046 A1 | 3/2011 |
| EP | 0466956 A1 | 1/1992 |
| FR | 2534066 A1 | 4/1984 |
| GB | 2049320 A | 12/1980 |
| JP | 2009142444 A | 7/2009 |
| JP | 2011518627 A | 6/2011 |
| WO | 9504501 A1 | 2/1995 |
| WO | 03007669 A1 | 1/2003 |
| WO | 2006057744 A2 | 6/2006 |
| WO | 2009132799 A2 | 11/2009 |

OTHER PUBLICATIONS

Birch et al., "A Contact X-Ray Therapy Unit for Intracavity Irradiation," Physics in Medicine and Biology, 35(2):275-280 (1990).

Fletcher et al., "An assessment of GafChromic film for measuring 50 kV and 100 kv percentage depth dose curves," Physics in Medicine and Biology, 53(11): N209-N218 (2008).

Eaton et al., "Dosimetry measurements with an intra-operative x-ray device," Physics in Medicine and Biology, 55(12): N359-N369 (2010).

* cited by examiner

APPARATUS AND METHOD FOR GENERATING X-RAY RADIATION

The present invention relates to an apparatus for generating X-ray radiation, in particular for generating an X-ray radiation field. Furthermore, the present invention also relates to a method for generating X-ray radiation, in particular for generating an X-ray radiation field.

Such apparatus and methods are for example used in the field of irradiation therapy by means of irradiation devices. Intraoperative irradiation is nowadays often carried out with modern irradiation devices, which allows for the radiation to be brought immediately to the location of irradiation, for example into a tumor or to a tumor bed.

Different kinds of applicators, for example spherical applicators and needle applicators, are currently being used for treatment of a patient by means of intraoperative irradiation devices. These applicators are supposed to generate an isotropic and homogeneous X-ray radiation field from the respective applicator surface or the isocentre of the location of generation of the X-ray radiation. An isotropic radiation is in particular such kind of radiation, which emits or is being emitted in all directions uniformly.

With intraoperative irradiation with said kinds of applicators it is in particular supposed to achieve that in the adjacent tissue of the tumor bed or in the tumor itself, respectively, from the applicator surface in all directions the at least approximately same depth dose rate curve is present, so that after a certain treatment time in each direction in the corresponding same depth the same dose has been applied. In such a case, the iso dose areas optimally are spheres with the centre being in the centre of the applicator or the isocentre, respectively.

The X-ray radiation or corresponding X-ray radiation fields, which are required for a respective irradiation, are usually generated in or by means of an X-ray radiation source. In particular, the X-ray radiation source is a component of the irradiation device. The operating principle of known X-ray radiation sources, for example for intraoperative irradiation, is in particular based on the fact, that electrons are being generated in an electron beam source and are being emitted as an electron beam. The electron beam is accelerated in an acceleration stage by means of an acceleration voltage, which in particular is high voltage. The thus generated and accelerated electron beam is directed onto a target, which may for example be made of gold. The target may for example be located in the tip of an applicator as described before. Upon impinging of the electron beam on the target, the X-ray radiation is being generated, which is then being emitted from the target in the shape of a resulting X-ray radiation field. Such an irradiation device is for example described in WO 2009/132799 A2.

In case of linear guiding of the electron beam, where the electrons would impinge on one single location on the target, a resulting X-ray radiation field would be generated, which is normally not spherically shaped. The shape of the X-ray radiation field—among other factors—is dependent on the materials used, the material distribution in the tip of the applicator, the shape and/or thickness of the target, the acceleration voltage, the current and the like.

In practice, a spherical X-ray radiation field is often desirable. A spherical X-ray radiation field is in particular a ball-shaped or approximately ball-shaped radiation field. A spherical X-ray radiation field can for example be achieved, if the electron beam is not directed to one point of the target but if the electron beam is deflected. For this purpose, as is already known from the above mentioned solution according to WO 2009/132799 A2, the electron beam may pass through a magnetic field, wherein the magnetic field is being generated by means of deflection coils. With the magnetic field, the electron beam can be deflected, whereby the impingement location of the electrons on the target may be varied.

Good results with respect to a spherical X-ray radiation field can be achieved, for example, if the electron beam is not directed to a single point of the target, but is guided approximately circularly over the surface of the target by means of the deflection coils. In order to achieve this spherical radiation field, currently, the electron beam is not directly guided in the forward direction onto the target, but is magnetically deflected by means of deflection coils, for example of x,y-coils, in such a way, that the electron beam describes a polygon (hexadecagon) on the target. That means, that the electronics guide the electron beam by means of the coils consecutively to 16 points, wherein the time which the electron beam requires for the change from one point to the next, is considerably shorter than the time within which the electron beam remains on one of these points. Therefore, on a picture taken with an X-ray camera with short period of exposure also no polygon but 16 corners can be identified. That means, that the intensity of radiation, which is generated at the connecting lines is negligible compared to the intensity which is generated at the corners.

Furthermore, currently, the same acceleration voltage is maintained during the entire irradiation, so that in all directions approximately the same depth dose curve is generated.

Ideally, the hexadecagon is the approximation of a circle. That means that the 16 corner points all have the same distance to the centre of the circle. The radius of this circle, however, is fixed. By measuring the radiation, the electron beam is controlled to each point of the hexadecagon such that the determined radius is observed.

In order to obtain a proof of the isotropic X-ray radiation field, the X-ray radiation source is measured in a water phantom by means of an ionisation chamber for different distances and angles, in particular measured with respect to the longitudinal axis, or measured before each treatment in the +-x, +-y and +-z direction.

However, the following problems arise:

The isotropy is considerably influenced by the thickness of the different inner and outer coatings, such as gold, Ni+CrN or CrN only, and the dimensions or the deviations thereof from the ideal shape, of the respectively mounted X-ray radiation source, in particular of the Be-tip (beryllium-tip) of the X-ray radiation source. This, however, cannot be corrected by the above mentioned method which is currently used. That means, that for example those X-ray radiation sources, which do not comply with the required specification of the isotropy during the measuring in the water phantom, have to be eliminated or scrapped.

If a non-spherical radiation field is required, wherein the radiation is not isotropic, for example for protection of deeper organs in a certain direction, currently a shield, for example a so called "spherical shield" has to be placed on the spherical applicator in the corresponding direction, whereby this shield, however, absorbs almost the entire radiation in this solid angle, which will hereinafter also be referred to as spatial angle, and the solid angle in addition is fixed by the size of the shield.

If a non-spherical radiation field is required, for example a flat field, the currently used method does not prove to be very useful, because a flat radiation field has to be formed by means of absorption bodies of complex shape from the isotropic radiation field. Therein only a narrow spatial angle of the spherical radiation field is used. The large remainder has to be absorbed by the applicator housing, in order to not endanger the patient and/or the environment. The radiation which is present in the spatial angle, which is used, is further weakened by the absorption bodies, which are used to that extent, that the desired flat radiation field is being generated. The dose rates of the applicators, which are necessary for that, for example of surface applicators, are thus low and the treatment time is correspondingly long.

Starting from the above mentioned state of the art, the present invention is based on the problem to further develop the initially mentioned apparatus and the initially mentioned method in such a way that the afore-described problems can be avoided.

The problem is solved according to the invention by the apparatus with the features according to independent claim 1 as well as by the method with the features of independent claim 10. Further features and details of the invention can be derived from the dependent claims, the description as well as from the drawings. Therein, features and details which are described in connection with the apparatus according to the invention apply with respect to their disclosure in their entirety also to the method according to the invention, so that statements made with respect to the apparatus also apply to their full extent to the method and vice versa.

The underlying concept of the present invention is that the generated X-ray radiation, in particular the generated X-ray radiation field can be influenced by varying at least one parameter of the electron beam source and/or of the electron beam.

According to the present invention in particular an X-ray radiation field is being generated, wherein the X-ray radiation field is formed by the entirety of the generated X-ray radiation. The shape and/or size of the resulting X-ray radiation field can now in particular be adjusted or can be adapted to a specification, by adjusting or setting at least one parameter of the electron beam source and/or of the electron beam, by means of which the resulting X-ray radiation field is generated.

According to the first aspect of the invention, an apparatus for generating X-ray radiation, in particular for generating an X-ray radiation field, is provided, comprising an electron source for generating an electron beam as well as a target for generating X-ray radiation, in particular an X-ray radiation field, by electrons of the electron beam impinging on the target. The apparatus is characterized according to the invention, in that it is designed for generating an adjustable and/or changeable X-ray radiation, in particular for generating an adjustable and/or changeable X-ray radiation field, and in that the apparatus has a variation appliance for varying at least one parameter of the electron beam source and/or of the electron beam in order to influence the X-ray radiation, in particular the X-ray radiation field.

According to the invention, an apparatus for generating X-ray radiation, in particular for generating an X-ray radiation field, is provided. Therein, the invention preferably relates to generating low-energy and/or soft X-ray radiation. The apparatus is preferably part of an irradiation apparatus.

The apparatus has an electron source. By means of the electron source, electrons are being generated, which are in particular emitted as an electron beam. The electron source thus in particular serves for generating an electron beam. In addition, the apparatus has a target, wherein the target may for example be made of gold. The target serves for the actual generation of X-ray radiation and/or of the X-ray radiation field. The electrons which are generated by the electron source impinge on the target as an electron beam. The X-ray radiation or the X-ray radiation field, respectively, which is emitted from the target, is generated by the electrons of the electron beam impinging on the target.

According to the invention, it is now provided, that this apparatus is designed for generating an adjustable and/or changeable X-ray radiation, in particular for generating an adjustable and/or changeable X-ray radiation field. This means, that the X-ray radiation and/or the X-ray radiation field can freely or arbitrarily be adjusted and/or changed by means of the apparatus.

For this purpose, according to the invention, it is provided, that the apparatus has a variation appliance. The variation appliance may also be referred to as variation means or a variation unit. Due to this variation appliance, it becomes possible, to influence the X-ray radiation, in particular the X-ray radiation field. According to the invention, it is furthermore provided, that the variation appliance is designed for varying at least one parameter of the electron beam source and/or of the electron beam.

A parameter of the electron beam source and/or the electron beam is in particular a characteristic value, by means of which in particular the generation of the electrons or of the electron beam and/or the properties of the generated electrons and/or of the electron beam and/or the path of the generated electrons and/or of the electron beam can be influenced. The present invention is not limited to certain parameters. Preferred but non-limiting examples of such parameters will be described in the further description in more detail.

The present invention is also not limited to certain embodiments of the variation appliance. The variation appliance may for example be a suitable device, of example a control device. It is, however, also possible that the variation appliance is a computing device. In a different embodiment, it may be provided that the variation appliance is software, a computer program product or the like.

The basic function of the variation appliance in any case is, that the variation appliance is designed such, that it can influence certain parameters of the electron beam source and/or of the electron beam.

The apparatus according to the invention as well as the method according to the invention, which will be described later, can in particular be used in the field of intraoperative irradiation. Therein, X-ray radiation, in particular X-ray radiation of short reach, is used, which is brought directly into the or to the irradiation location, for example a tumor or to the tumor bed. In an X-ray radiation source, which is used, electrons are generated in an electron source. The electrons are accelerated as an electron beam by means of an acceleration voltage to a target, for example made of gold. This is where the in particular low-energy X-ray radiation is being generated, which is in particular isotropically emitted and penetrates into the tissue, which is to be irradiated.

X-ray probes, which have a tip made of beryllium, are often being used for such an irradiation therapy. Beryllium is material which is almost transparent for X-ray radiation. The X-ray probe is preferably designed as an evacuated electron beam tube. In this electron beam tube, a beam of electrons is generated by means of the electron source, which is then being accelerated by means of an acceleration voltage. The electron beam is directed towards the target. On the target, the electrons are abruptly slowed down and X-ray radiation is being generated.

The apparatus according to the invention can therefore preferably have an X-ray probe with an evacuated tube and with a target arranged therein as well as an electron source. In addition, an acceleration appliance for accelerating the electrons by means of an acceleration voltage, which may also be referred to as electron accelerator, may be provided. The acceleration appliance or accelerator may also be referred to as an acceleration unit or acceleration means. The acceleration of the electrons is effected in particular by means of high voltage, which is applied at the acceleration appliance. Such an acceleration appliance will be described in more detail in the following description.

Furthermore, a deflection appliance for deflecting the electron beam on its path to the target may be provided. Such a deflection appliance may also be referred to as deflection means or a deflection unit and will be described in more detail in the following description.

The variation appliance is in particular designed for adjusting and/or changing the emission characteristics of the X-ray radiation, which is emitted from the target, in particular of the X-ray radiation field, which is emitted from the target. By means of the variation appliance, it is now possible to change the emission characteristics. The X-ray radiation field, which is being generated and emitted from the target, is being varied, by changing at least one parameter of the electron beam source and/or of the electron beam. Thus the electron beam is varied, in order to influence the resulting X-ray radiation field.

Preferably, the variation appliance is designed for influencing the isotropy of the X-ray radiation, in particular for influencing the isotropy of the X-ray radiation field. An isotropic radiation is, as already described, radiation, which emits in all directions equally and/or which is emitted in all directions equally. With the present invention it is now possible that the isotropy of the X-ray radiation field can be adapted, for example to changing conditions, to certain specifications and the like. Specifications may also be referred to as pre-settings. In particular, an isotropy adaption of the resulting, emitted X-ray radiation field can be achieved by controlling the electron beam current by the variation appliance.

Preferably, the variation appliance may have a control appliance for controlling the electron beam source and/or the electron beam. A control appliance of the electron beam is thus implemented in the variation appliance. The control appliance may also be referred to as control means or a control unit. By means of the control appliance, the electron beam may preferably be controlled in such a way, that an X-ray radiation field with any desired distribution is generated. The control appliance may be software, a computer program product and the like. Such control may preferably be carried out by using appropriate control algorithms. Such control algorithms, which are also referred to as intelligent control algorithms, may for example determine, calculate and amend individual parameters of the electron source and/or of the electron beam.

Preferably, the variation appliance is designed for varying at least one parameter of the electron beam source and/or of the electron beam regarding the spatial influencing of the X-ray radiation beam, in particular of the X-ray radiation field. This means, that the influencing is effected spatially.

In a further embodiment, the variation appliance is designed for adjusting and/or changing the emission characteristics of the X-ray radiation emitted from the target, in particular of the X-ray radiation field emitted from the target. In such a case, it is in particular provided, that the variation appliance is designed for varying at least one parameter of the electron beam source and/or of the electron beam, while the electron beam is impinging on the target, in particular during a course of the electron beam on the target. The course of the electron beam on the target may also be referred to as a loop. Thereby, it also becomes in particular possible with the present invention, that the generated X-ray radiation, in particular the generated X-ray radiation field, may be influenced also during the operation of the apparatus or of an irradiation appliance provided with the apparatus, for example in real time or close to real time.

With the apparatus according to the invention, in particular the emission characteristics of the X-ray radiation, which is emitted from the target, can be changed, by varying parameters of the electron beam source and/or the electron beam during impinging of the electron beam on the surface of the target, in particular during the course of the electron beam on the surface of the target.

In this respect the invention is not limited to certain parameters. Some advantageous but non-limiting examples thereof will be described later in more detail.

Preferably, it is provided, that the apparatus has a deflection appliance for deflecting the electron beam. The deflection appliance may for example be magnetic deflection coils. By means of the magnetic deflection coils a magnetic field may be created, in order to deflect the electrons of the electron beam, which are accelerated towards the target. This allows setting the location at which the electrons impinge on the target. Thereby, in particular the spatial radiation profile of the generated and emitted X-ray radiation can be adjusted. By means of the deflection appliance, for example the deflection coils, the electron beam may be moved over the target.

The variation appliance is in particular designed for operating the deflection appliance. That means for example, that the variation appliance is designed to handle the magnetic deflection coils in such a way, that a desired magnet field is created by them. Therein, the operation of the deflection appliance via the variation appliance is preferably effected in such a way, that by actuating the deflection appliance, at least one parameter of the electron beam, in particular the coordinates of the electron beam on the target and/or the impingement location of the electron beam on the target and/or the impingement path of the electron beam on the target and/or the radius of the course of the electron beam on the target and/or the residence time of the electron beam on a point of the target is/are varied or may be varied, in particular during the course of the electron beam on the target.

By this preferred embodiment, in particular a departure from a fixed specification of a radius and/or a shape, for example a polygon, and/or of a path and/or of the impingement location of the electron beam on the target become possible. In particular, it becomes possible, that the coordinates of the electron beam can be varied, in particular in real time, on the target surface.

Also the residence time of the electron beam at one point of the target before the electron beam is guided to the next point on the target can be changed. With the described preferred embodiment therefore also a departure from fixed time durations for impingement points of the electron beam on the target becomes possible, so that for different directions for example different depths dose curves can be generated.

In a further embodiment, the apparatus preferably has an acceleration appliance for accelerating the electrons by means of an applied acceleration voltage. The acceleration appliance is preferably an electron accelerator, which provides an acceleration voltage, in particular a high voltage, by means of which the electrons of the electron beam are accelerated.

Preferably, the variation appliance is designed for actuating and/or operating the acceleration appliance. That means for example, that the variation appliance is designed to handle the acceleration appliance in a way that the desired acceleration voltage is provided by the acceleration appliance. The actuation of the acceleration appliance via the variation appliance is preferably effected such, that the acceleration voltage for accelerating the electron beam which impinges on the target is varied or may be varied, in particular during the course of the electron beam on the target, by actuating the acceleration appliance.

By means of this preferred embodiment, in particular a departure from a fixed acceleration voltage for all impingement points of the electron beam on the target becomes possible, so that in particular for different directions different depth dose curves can be generated. That means, that the variation appliance is preferably designed to actuate the acceleration appliance in such a way, that—via this acceleration appliance—the electron beam is accelerated with different acceleration voltages towards the target, in particular during the course of the electron beam on the target.

By varying the acceleration voltage it is achieved, that the electron beam impinges on the target with differing energy. By departing from fixed acceleration voltages for all impingement points of the electron beam on the target, a variation of the acceleration voltage during the course of the electron beam on the target becomes possible, so that different depth dose curves for different directions can be achieved.

The present invention is not limited to certain acceleration voltages. Preferably, an acceleration voltage between 0 and 150 kV is applied. For irradiation of tissue preferably an acceleration voltage between 10 and 100 kV is applied.

As a further parameter which may be influenced by the variation appliance, for example the amperage may be mentioned.

Preferably, the variation appliance has an interface for receiving external specification values and/or reference values for the generation of a defined X-ray radiation, in particular for generating a defined X-ray radiation field and/or for varying of at least one parameter of the electron beam source and/or of the electron beam. The specification and/or reference values are transmitted via the interface, in particular from externally, to the comparison device.

Alternatively or additionally, the variation appliance may have an input appliance for input of specification values and/or reference values for the generation of a defined X-ray radiation, in particular for generating a defined X-ray radiation field and/or for varying at least one parameter of the electron beam source and/or the electron beam. Such an input appliance may for example be a key board, a touch panel, a reading device for reading in data and the like. If the variation appliance is software or a computer program product, the input appliance may for example be an input window, where specification values are put in.

The specification values and/or reference values may for example be values for a desired distribution of the X-ray radiation field. In a different embodiment, the specification values and/or reference values may be feedback of isotropy measuring values.

Thereby options for influencing the electron beam can be provided which are not only based on measurements at the apparatus for generating the X-ray radiation but which also allows a feedback, in particular a control feedback by external devices, for example measuring devices. Such measuring devices may for example be a water phantom or a PDA expanded by several spatial directions.

With the described embodiments, it becomes in particular possible, that the emission characteristics of the X-ray radiation, in particular of the X-ray radiation field, which is emitted from the target, can be adapted to a specification. This may be understood for example as giving specification values and/or reference values in any desired way. This may for example be effected such, that by means of a calculation program, which may be a simulation program, suitable specification values and/or reference values are determined. Those can then be used for influencing the X-ray radiation and/or the X-ray radiation field. The present invention is also not limited with respect to the specification to specific kinds of specification.

In a further embodiment, the variation appliance preferably has a calculation unit for calculating and/or generating specifications for varying of at least one parameter of the electron beam source and/or of the electron beam from the specification values and/or reference values. Alternatively or additionally, it is preferably provided, that the variation appliance has an implementing appliance for varying at least one parameter of the electron beam source and/or of the electron beam with respect to the calculated or generated specification or the received and/or input specification values and/or reference values.

Thereby, in particular the possibility of training the apparatus for generating X-ray radiation for the respectively desired case is provided. For example, by measuring and feeding back of respective specification values and/or reference values with the variation appliance it may be achieved, that a defined X-ray radiation field is generated by different impingement points of the electron beam on the target with different acceleration voltages and different residence times.

It may for example be provided that by means of an external measuring setup, the isotropy of the X-ray radiation source is determined. The isotropy values which are obtained thereby, may be read out from the measuring setup and may be transmitted to the variation appliance. Thereby, the measuring values, for example the isotropy measuring values, are fed back into the variation appliance, for example control algorithm software. In the variation appliance the new electron beam parameters for this new X-ray radiation field distribution are then calculated. Subsequently, the electron beam and/or the electron source may be actuated or controlled with these new parameters by means of the variation appliance.

Preferably, the resulting X-ray radiation field can be detected or determined and can be compared to an X-ray radiation field, which is adjusted or adapted to a specification, by means of a comparison appliance. Preferably, with the deviation from the determined X-ray radiation field from the adjusted X-ray radiation field or X-ray radiation field adapted to a specification, a correction of the determined X-ray radiation field is effected.

The determined specification values and/or reference values can be stored in or into a storage appliance. For this purpose it is preferably provided, that the apparatus for generating X-ray radiation, in particular the variation appliance, has such a storage appliance or can at least access such a storage appliance via an interface. Correspondingly, the parameters, which have been determined by the variation appliance or comparison appliance and which are changed by means of the variation appliance, can be stored in or into the storage appliance. A variation of the parameters can then be effected with these stored values.

With the apparatus according to the first aspect of the invention in particular an intelligent influencing of the resulting X-ray radiation, in particular the resulting X-ray radiation field, can be achieved by influencing the electron source and/or the electron beam, in order to generate any desired X-ray radiation field distribution, in particular with a feedback of isotropy measuring values.

In particular, also a loop process is possible in order to continuously improve the X-ray radiation field distribution. A fully automated control of the process of improvement of the X-ray radiation field distribution is possible and is preferably provided.

The actuation of the apparatus for generating X-ray radiation or of the X-ray radiation source can—besides a fully automated actuation—also be effected semi-automatic or manually. The actuation can also be effected digitally or analogous.

Variations are also possible with respect to the embodiment and/or construction type and/or platform of the processor and/or computer, whereon the software is supposed to run. The present invention is also not limited to a certain programming language, in which the software is written. Furthermore, the invention is not limited to a specific Graphic-User-Interface (GUI) embodiment in the software. The operating system, whereon the software runs, as well as the layout of the apparatus for generating X-ray radiation or of the X-ray radiation source, which is supposed to generate the radiation, are also not fixed and may obviously be adapted.

With the apparatus according to the first aspect of the invention, the variation of the resulting X-ray radiation and/or of the resulting X-ray radiation field, in particular of the emission characteristics, can be effected before and during the generation of the X-ray radiation field. Obviously, it is also possible, that the adjustment or setting of the X-ray radiation field can first be effected before the generation of the X-ray radiation field. If during the irradiation, a change of the X-ray radiation field is to be effected, this change can also be performed. It is also possible, that the X-ray radiation field is stored for example in a file, for example as a specification, because it has already been used in an earlier irradiation. The shape of such an X-ray radiation field does then not necessarily have to be adjusted before generating the X-ray radiation field. In such a case it may be sufficient that the X-ray radiation field is adjusted, that means changed, during the provisioning and/or irradiation. The present invention is not limited to a specific approach in this respect.

According to a second aspect of the invention a method for generating an adjustable and/or changeable X-ray radiation, in particular for generating an adjustable and/or changeable X-ray radiation field, is provided, wherein by means of an electron source an electron beam is generated, wherein the electron beam is being directed towards a target and wherein an X-ray radiation, in particular an X-ray radiation field, is generated by electrons of the electron beam impinging on the target. The method is characterized in that by means of a variation appliance at least one parameter of the electron beam source and/or of the electron beam is varied, that the X-ray radiation, in particular the X-ray radiation field, is influenced by means of the variation of the at least one parameter and in that in particular the emission characteristics of the X-ray radiation, in particular of the X-ray radiation field, from the target are changed by means of the variation of the at least one parameter.

In particular, the method may be performed by means of an apparatus for generation of X-ray radiation according to the invention, which has been described above, so that with respect to the disclosure relating to the layout and functioning of the method full reference is also made to the description of the apparatus of the invention and is incorporated by reference.

Preferably, as already explained above, the electron beam source and/or the electron beam is controlled by means of a variation appliance.

In a further embodiment, as already explained above, the isotropy of the X-ray radiation, in particular the isotropy of the X-ray radiation field is influenced by means of the variation appliance.

By means of the variation appliance, as already explained above, at least one parameter of the electron beam source and/or of the electron beam with respect to the spatial influencing of the X-ray radiation, in particular of the X-ray radiation field, is influenced.

By means of the variation appliance in particular an adjustment and/or changing of the emission characteristics of the X-ray radiation emitted from the target, in particular the X-ray radiation field emitted from the target, is effected. Therein, it may be provided, as already described above, that by means of the variation appliance a variation of at least one parameter of the electron beam source and/or of the electron beam is effected during the impingement of the electron beam on the target, in particular during the course of the electron beam on the target.

Preferably, it is provided, that by means of the variation appliance a deflection appliance for deflecting the electron beam is actuated and that by actuation of the deflection appliance at least one parameter of the electron beam, in particular the coordinates of the electron beam on the target and/or the impingement location of the electron beam on the target and/or the impingement path of the electron beam on the target and/or the radius of a course of the electron beam on the target and/or the residence duration of the electron beam on a point of the target is varied or may be varied.

In a further embodiment it is preferably provided, that by means of the variation appliance an acceleration appliance for accelerating the electrons by means of an applied acceleration voltage is actuated and that by means of actuation of the acceleration appliance the acceleration voltage for acceleration of the electron beam, which impinges in the target, is varied.

Preferably, it is further provided that via an interface external specification values and/or reference values for the generation of a defined X-ray radiation, in particular a defined X-ray radiation field, and/or for varying of at least one parameter of the electron beam source and/or of the electron beam are received in the variation appliance, and/or that by means of an input appliance specification values and/or reference values for generation of a defined X-ray radiation, in particular a defined X-ray radiation field and/or for varying at least one parameter of the electron beam source and/or of the electron beam are input into the variation appliance and that on the basis of the received and/or input specification values or of a specification which has been calculated there from in the variation appliance by means of the variation appliance at least one parameter of the electron beam source and/or of the electron beam is influenced.

It may for example be provided, that via an external measuring setup the isotropy of the X-ray radiation source is determined. The thus obtained isotropy values may be read out of the measuring setup and may be transmitted to the variation appliance. Thereby, the measuring values, for example the isotropy measuring values, are fed back into the variation appliance, for example control algorithm software. In the variation appliance then the new electron beam parameters for the new X-ray radiation field distribution are calculated. Subsequently, the electron beam and/or the electron source can be actuated by means of the variation appliance with these new parameters.

With the present invention according to the above described invention aspects it in particular becomes possible to change the emission characteristics of X-ray radiation, in particular of an X-ray radiation field, by varying parameters of the electron beam source and/or the electron beam, in particular during a course of the electron beam on the target. Such parameters can in particular be the acceleration voltage and/or amperage and/or the impingement location and/or the impingement path of the electron beam on the target and/or the residence time of the electron beam on a location on the target and the like, wherein the invention is not limited to these mentioned parameters.

With the present invention is made possible in a simple way to adjust a resulting X-ray radiation field with any desired emission characteristics, in particular of any desired shape and/or size. Thereby, the irradiation of a substrate can be optimized, as the substrate will for example only be irradiated at locations, which are supposed to be irradiated. This adjustment and/or setting of the emission characteristics of the X-ray radiation field is effected without mechanical shielding, but by adjusting parameters, which determine the radiation field. These parameters, which determine the radiation field, can for example be calculated by intelligent control algorithms. The calculation may for example be carried out in a calculation or processing unit.

The invention will now be explained in more detail with respect to exemplary embodiments with reference to the enclosed drawings, wherein.

Figure 1:
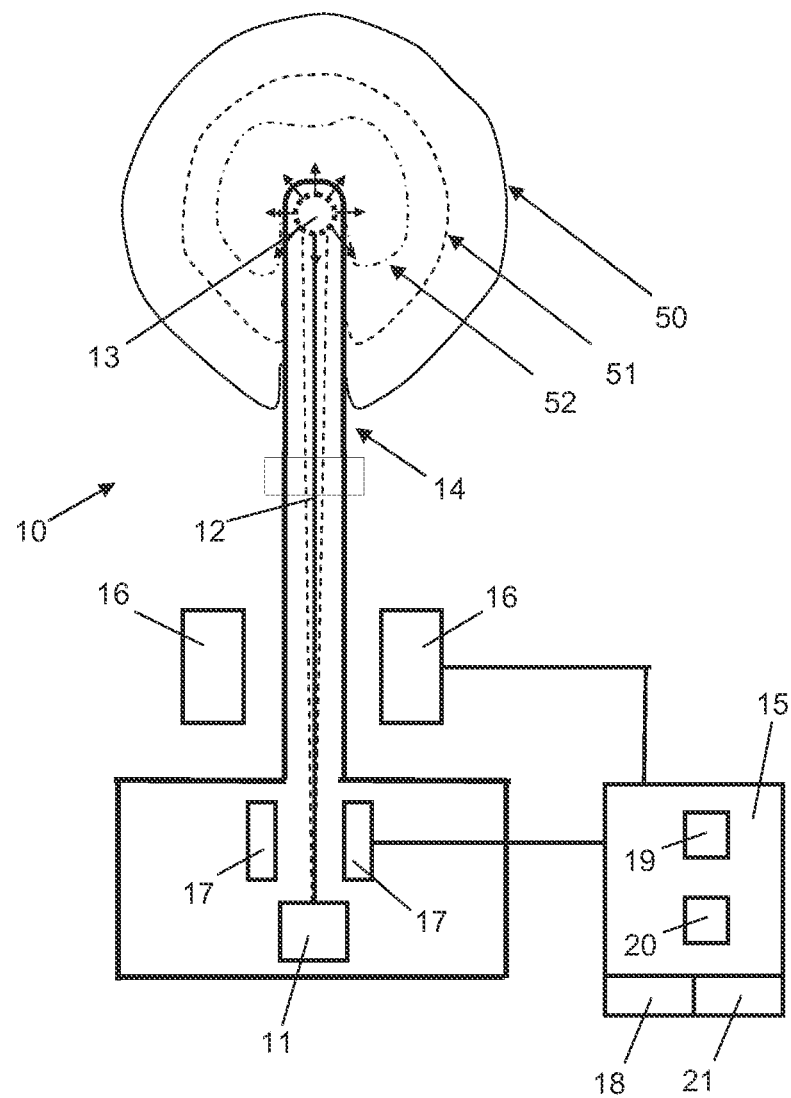
FIG. 1 shows a depiction of an apparatus for generating X-ray radiation, in particular an X-ray radiation field, according to the invention.

In the figures an apparatus 10 for generating an X-ray radiation, in particular for generating an X-ray radiation filed, is shown. The apparatus is in particular used in the field of intraoperative irradiation.

The apparatus 10 has an electron source 11. By means of the electron source 11 electrons are generated, which in particular are emitted as an electron beam 12. The electron source 11 in particular servers for generating an electron beam 12. Furthermore, the apparatus has a target 13, wherein the target may for example be made of gold. The target 13 serves for the actual generation of the X-ray radiation and/or X-ray radiation field, which is clarified by the arrows pointing away from the target 13. The target 13 is arranged in an evacuated tube 14 of an X-ray probe at its distal end.

The electrons, which are generated by the electron source 11, impinge on the target 13 as an electron beam 12. There, the electrons of the electron beam 12 are slowed down, whereby the X-ray radiation and/or the X-ray radiation field is generated, which is emitted from the target 13.

According to the invention it is now provided, that this apparatus 10 is designed for generating an adjustable and/or changeable X-ray radiation, in particular for generating an adjustable and/or changeable X-ray radiation field. This means that by means of the apparatus 10, the X-ray radiation and/or the X-ray radiation field and/or their emission characteristics may be adjusted or changed freely or user-defined.

For this purpose it is provided, that the apparatus 10 has a variation appliance 15. By means of this variation appliance 15 it becomes possible, to influence the X-ray radiation, in particular the X-ray radiation field. According to the invention it is further more provided, that the variation appliance 15 is designed for varying at least one parameter of the electron beam source 11 and/or of the electron beam 12.

Furthermore it is provided, that the apparatus 10 has a deflection appliance 16 for deflecting the electron beam 12. The deflection appliance 16 may be for example magnetic deflection coils. By means of the deflection appliance 16, a magnetic field can be created, in order to deflect the electrons of the electron beam 12, which are accelerated towards the target 13, which is indicated by the dashed lines of the electron beam. This allows for setting the location, where the electrons impinge on the target 13. Thereby, in particular the spatial radiation profile of the generated and emitted X-ray radiation can be adjusted. By means of the deflection appliance 16, the electron beam 12 can be moved over and on the target 13.

The variation appliance 15 is designed for actuating the deflection appliance 16, which is clarified by the corresponding connecting line in FIG. 1. This means for example that the variation appliance 15 is designed to actuate the deflection appliance 16 in such a way, that thereby a desired magnetic field is created. The actuation of the deflection appliance 16 by means of the variation appliance 15 preferably is effected such, that by actuation of the deflection 16 at least one parameter of the electron beam 12, in particular the coordinates of the electron beam 12 on the target 13 and/or the impingement location of the electron beam 12 on the target 13 and/or the impingement path of the electron beam 12 on the target 13 and/or the radius of the course of the electron beam 12 on the target 13 and/or the residence period of the electron beam on a point of the target 13 are varied, in particular during the course of the electron beam 12 on the target 13.

In addition, the apparatus 10 has an acceleration appliance 17 for accelerating the electrons by means of an applied acceleration voltage, in particular a high voltage. The variation appliance 15 is designed for actuating the acceleration appliance 17, which is depicted in FIG. 1 by the corresponding connecting line. This means, that the variation appliance 15 is designed to handle the acceleration appliance 17 in such a way, that by the acceleration appliance 17 a desired acceleration voltage is provided. The actuation of the acceleration appliance 17 via the variation appliance 15 is effected such, that by actuating the acceleration appliance 17 the acceleration voltage for accelerating the electron beam 12, which impinges on the target 13, is varied, in particular during the course of the electron beam 12 on the target 13.

The apparatus 10, which in its entirety can also be referred to as X-ray radiation source, is used to generate and/or provide an X-ray radiation field 50, 51, 52, so that a substrate, for example in tissue, (not shown) can be irradiated.

As depicted in FIG. 1, the X-ray radiation field 50, 51, 52 propagates spherically or approximately spherically. The centre of the X-ray radiation field 50, 51, 52 is the target 13, at which the resulting X-ray radiation and/or X-ray radiation field is being generated. The centre of the X-ray radiation field 50, 51, 52 is also referred to as the isocentre. The spherical distribution of the X-ray radiation field 50, 51, 52 is indicated in FIG. 1 by corresponding isotropy lines. Isotropy line in general refers to a line where the same isotropy, that means values of the same radiation, is present. The isotropy lines in FIG. 1 thus show lines, where the same radiation is present.

By means of an apparatus 10, which generates such an X-ray radiation field 50, 51, 52, in general the irradiation of substrates, in particular of tissue is possible. If the substrate, which is to be irradiated, is, however, sensitive substrate and/or the irradiation is supposed to be effected in a defined depth or in a defined distance to the substrate surface, it may be necessary that certain tissue locations and/or neighbouring tissue are not to be influenced by the irradiation. Simply put, it may be desired that tissue locations, which may for example be in immediate vicinity to the location, which is to be irradiated, are not to be irradiated.

Figure 2:
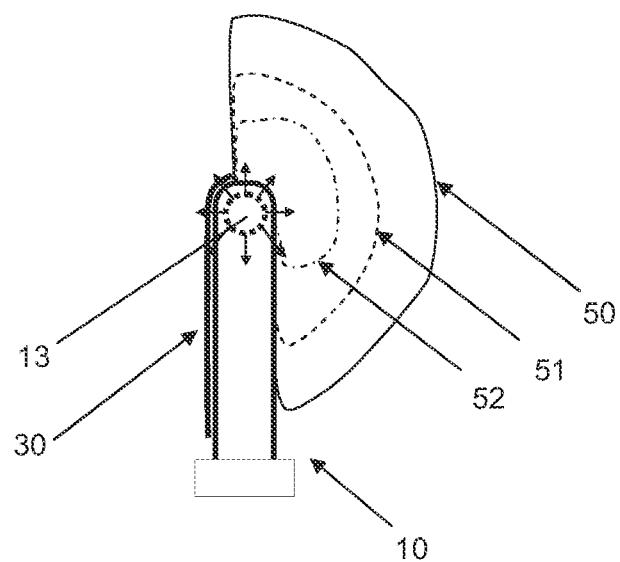
FIG. 2 shows a section of a depiction of an apparatus for generating an X-ray radiation, in particular an X-ray radiation field, which emits radiation, wherein a mechanical shielding for influencing the resulting X-ray radiation field is provided.

In order to solve such a task, nowadays so called mechanical shielding 30 is being used. In FIG. 2 besides a radiation source 11 a mechanical shielding 30 for influencing the X-ray radiation field 50, 51, 52 is shown.

The basic principle of the apparatus 10 shown in FIG. 2 corresponds to the one of the apparatus 10 of FIG. 1, so that reference is made to the corresponding description above and is incorporated by reference herewith.

By using a mechanical shielding 30 the X-ray radiation field 50, 51, 52 can be influenced accordingly.

In FIGS. 1 and 2 only a two-dimensional depiction of an X-ray radiation field 50, 51, 52 is shown. It is, however, obvious that the depiction is a simplified depiction and that the propagation of the X-ray radiation field 50, 51, 52 can also occur in three spatial directions, that means three-dimensionally.

With the mechanical shielding 30 the X-ray radiation field 50, 51, 52, which is shown in FIG. 2, is influenced in such a way, that the X-ray radiation field 50, 51, 52 at the location, where the mechanical shielding is positioned or arranged does not exit from the apparatus 10. By this hindrance of emission or propagation of the X-ray radiation field 50, 51, 52, tissue, which is at this location, can be protected from the radiation or the X-ray radiation field 50, 51, 52.

On the side, which is not covered or shielded by a or the mechanical shielding 30, the X-ray radiation field 50, 51, 52 can propagate similar to the propagation or distribution as shown in FIG. 1.

The option of influencing the X-ray radiation field 50, 51, 52 by using a mechanical shielding 30, as shown in FIG. 2, has the disadvantage, that an additional component is necessary. In addition, it is disadvantageous when using a mechanical shielding 30, that for example the shape and/or size of the X-ray radiation field 50, 51, 52 can only be changed, by using a mechanical shielding 30, which is designed differently.

These problems can for example be avoided, by adjusting or adapting the shape and/or size of the resulting X-ray radiation field 50, 51, 52, which is emitted from the target 30, by means of the apparatus 10, which is depicted and has been described with respect to FIG. 1, to specifications, by varying before and/or during the generation and/or provisioning of the X-ray radiation field 50, 51, 52 via the variation appliance 15 at least one parameter of the electron source 11 and/or of the electron beam 12. Thereby, the emission characteristics of the resulting X-ray radiation or of the resulting X-ray radiation field 50, 51, 52 are influenced.

Figure 3:
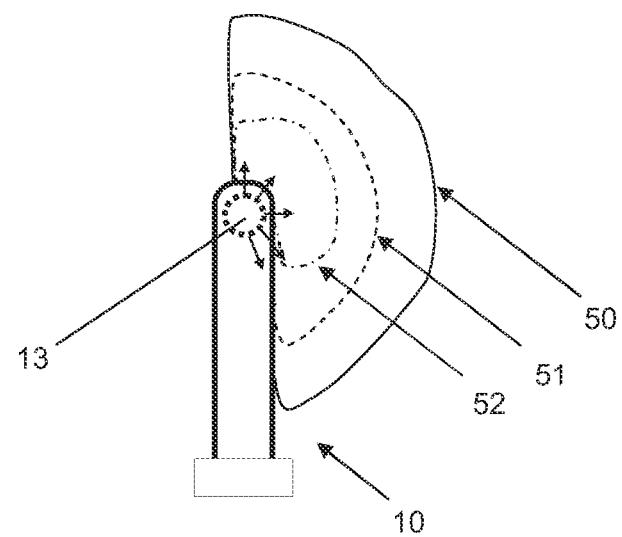
FIG. 3 shows a depiction of an apparatus according to FIG. 2, wherein the method according to the invention is being used.

Such an embodiment is shown in FIG. 3. FIG. 3 is, however, a mere schematic depiction for clarifying the operating principle of the apparatus 10 according to the invention as well as of the method according to the present invention.

For reasons of simplification and for a better comparison, an X-ray radiation field 50, 51, 52 is shown in FIG. 3, which corresponds to the X-ray radiation field 50, 51, 52 of FIG. 2. In FIG. 3, as an example, an X-ray radiation field 50, 51, 52 is supposed to be generated or provided by means of the apparatus 10 shown in FIG. 1 and utilizing the variation appliance 15, which X-ray radiation field 50, 51, 52 is equal to or corresponds to the X-ray radiation field 50, 51, 52 of FIG. 2.

For this purpose, parameters of the electron source 11 and/or of the electron beam 12, which determine the radiation field, are adjusted or defined by means of the variation appliance 15 such, that the desired X-ray radiation field 50, 51, 52 is generated or provided.

If the acceleration voltage, which is necessary for generation a radiation dose rate and thus also for the generation of the X-ray radiation field 50, 51, 52, is changed, besides the shape and/or size of the X-ray radiation field 50, 51, 52, also the radiation intensity, the radiation dose rate and/or the radiation dose rate curve can be adjusted or freely selected.

Via the interface 18 of the variation appliance 15, which is shown in FIG. 1, the variation appliance 15 can receive values from outside, for example can receive external measuring values, which can be used for variation of the parameters of the electron source 11 and/or of the electron beam 12. Alternatively or additionally, such values can also be input or read in via an input appliance 21 of the variation appliance 15. These external measuring values can thus be used for influencing the resulting X-ray radiation, in particular the resulting X-ray radiation field, in particular their emission characteristics.

As further shown in FIG. 1, the variation appliance 15 has a calculation appliance 19 for calculating and/or generating a specification for varying of at least one parameter of the electron beam source 11 and/or of the electron beam 12 from specification values and/or reference values. Alternatively or additionally, it is preferably provided, that the variation appliance 15 has an implementing appliance 20 for varying at least one parameter of the electron beam source 11 and/or of the electron beam 12 with respect to the calculated and/or generated specification or received and/or input specification values and/or reference values.

Thereby, in particular the possibility of "training" the apparatus 10 for generating the X-ray radiation to the respectively desired case is given. For example, it may be achieved by measuring and feeding back of corresponding specification values and/or reference values with the variation appliance 15, by different impingement points of the electron beam 12 on the target 13 at different acceleration voltages and different residence times, to generate a predetermined X-ray radiation field 50, 51, 52.

For example it may be provided, that via an external measuring setup (not shown), the isotropy of the X-ray radiation source is determined. The thus obtained isotropy values can be read out from the measuring setup and can be transmitted to or input into the variation appliance 15 via the interface 18 or the input appliance 21. Thereby, the measuring values, for example isotropy measuring values, are fed back into the variation appliance 15, for example control algorithm software. In the variation appliance 15, the new parameters of the electron beam 12 are then calculated for this new X-ray radiation field distribution. Subsequently, the electron beam 12 and/or the electron source 11 is controlled by means of the variation appliance 15 with these new parameters.

REFERENCE NUMBERS

10 Apparatus for generating X-ray radiation, in particular for generating an X-ray radiation field
11 Electron source
12 Electron beam
13 Target
14 Tube of an X-ray probe
15 Variation appliance
16 Deflection appliance
17 Acceleration appliance
18 Interface
19 Calculation appliance
20 Implementing appliance
21 Input appliance
30 Mechanical shield
50 X-ray radiation field (propagation)
51 X-ray radiation field (propagation)
52 X-ray radiation field (propagation)

The invention claimed is:

1. Apparatus for generating an X-ray radiation field, comprising an electron beam source for generation of an electron beam as well as one target for generating the X-ray radiation field by electrons of the electron beam impinging on said target and being emitted from said target as X-ray radiation, said X-ray radiation field being formed by the entirety of the emitted X-ray radiation from said target, characterized in that, the apparatus is designed for generating an adjustable and/or changeable X-ray radiation field, and in that the apparatus has a variation appliance for varying at least one parameter of the electron beam source and/or the electron beam for spatially influencing the X-ray radiation field, said variation appliance being designed for varying parameters of the electron beam source and/or of the electron beam while the electron beam is impinging on the target during a loop of the electron beam on said target.

2. Apparatus according to claim 1, characterized in that the variation appliance is designed for influencing the isotropy of the X-ray radiation field.

3. Apparatus according to anyone of claim 1 or 2, characterized in that the variation appliance has a control appliance for controlling the electron beam source and/or the electron beam.

4. Apparatus according to claim 1, characterized in that the variation appliance is designed for adjusting and/or changing the emission characteristics of the X-ray radiation field emitted from the target.

5. Apparatus according to claim 1, characterized in that the apparatus has a deflection appliance for deflecting the electron beam and that the variation appliance is designed for actuating the deflection appliance such that by actuating the deflection appliance at least one parameter of the electron beam, in particular the coordinates of the electron beam on the target and/or the impingement location of the electron beam on the target and/or the impingement path of the electron beam on the target and/or the radius of a course of the electron beam on the target and/or the residence time of the electron beam at a point of the target is/are varied or is/are variable.

6. Apparatus according to claim 1 characterized in that the apparatus has an acceleration appliance for accelerating the electrons by means of an applied acceleration voltage and in that the variation appliance is designed for actuating the acceleration appliance such that by actuating the acceleration appliance the acceleration voltage for accelerating the electron beam, which impinges on the target, is varied or is variable.

7. Apparatus according to claim 1, characterized in that the variation appliance has an interface for receiving external specification values and/or reference values for generating a defined X-ray radiation field and/or for varying of at least one parameter of the electron beam source and/or of the electron beam and/or has an input appliance for input of specification values and/or reference values for generating a defined X-ray radiation field and/or for varying at least one parameter of the electron beam source and/or of the electron beam.

8. Apparatus according to claim 7, characterized in that the apparatus has a calculation appliance of calculating and/or generating of specifications for varying of at least one parameter of the electron beam source and/or of the electron beam from the specification values and/or reference values and/or that the variation appliance has an implementing appliance for varying at least one parameter of the electron beam source and/or the electron beam in respect of the calculated and/or generated specification or the received and/or input specification values and/or reference values.

9. Method for generating an adjustable and/or changeable X-ray radiation field, wherein by means of an electron beam source an electron beam is generated, wherein the electron beam is directed to one target and wherein by means of the electrons of the electron beam impinging on said target which emit from said target as an X-ray radiation, an X-ray radiation field is generated, said X-ray radiation field being formed by the entirety of the emitted X-ray radiation, characterized in that, by means of a variation appliance at least one parameter of the electron beam source and/or of the electron beam is varied, in that by means of the variation of the at least one parameter, the X-ray radiation field is spatially influenced and in that by means of the variation of the at least one parameter the emission characteristics of the X-ray radiation field, from the target is changed while the electron beam is impinging on the target during a loop of the electron beam on said target.

10. Method according to claim 9, characterized in that by means of the variation appliance, the electron beam source and/or the electron beam is controlled.

11. Method according to anyone of claim 9 or 10, characterized in that by means of the variation appliance a deflection appliance for deflecting the electron beam is actuated, and in that by means of the actuation of the deflection appliance at least one parameter of the electron beam, in particular the coordinates of the electron beam on the target and/or the impingement location of the electron beam on the target and/or the impingement path of the electron beam on the target and/or the radius of a course of the electron beam on the target and/or the residence period of the electron beam on one point of the target is/are varied.

12. Method according to claim 9, characterized in that by means of the variation appliance an acceleration appliance for acceleration of the electrons by means of an applied acceleration voltage is actuated and in that by the actuation of the acceleration appliance the acceleration voltage for acceleration of the electron beam which impinges on the target is varied.

13. Method according to claim 9, characterized in that via an interface external specification values and/or reference values for generating a defined X-ray radiation field, and/or for varying of at least one parameter of the electron beam source and/or of the electron beam are received in the variation appliance and/or that via an input appliance specification values and/or reference values for generating a defined X-ray radiation field, and/or for varying of at least one parameter of the electron beam source and/or of the electron beam are input into the variation appliance and in that on the basis of the received and/or input specification values or a specification which is calculated in the variation appliance there from, by means of the variation appliance at least one parameter of the electron beam source and/or of the electron beam is influenced.

14. Method according to claim 9, characterized in that it is carried out by an apparatus according to claim 1.

* * * * *